(12) United States Patent
Delaney, Jr. et al.

(10) Patent No.: US 11,213,596 B2
(45) Date of Patent: Jan. 4, 2022

(54) RADIOCONTRAST AGENTS, SCAVENGING METHODS, AND SCAVENGING SYSTEM

(71) Applicant: Boston Scientific Scimed, Inc., Maple Grove, MN (US)

(72) Inventors: Joseph Thomas Delaney, Jr., Minneapolis, MN (US); Douglas Dean Pagoria, Evergreen, CO (US); Richard Lee Tadsen, Roseville, MN (US); Andrew J. Ro, Plymouth, MN (US); Joel T. Eggert, Plymouth, MN (US); Douglas Pennington, Stillwater, MN (US); Paul Sorajja, Minneapolis, MN (US); Sarah Melissa Gruba, Vadnais Heights, MN (US); Tatyana Dyndikova, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/276,174

(22) Filed: Feb. 14, 2019

(65) Prior Publication Data

US 2019/0275178 A1    Sep. 12, 2019

Related U.S. Application Data

(60) Provisional application No. 62/641,682, filed on Mar. 12, 2018.

(51) Int. Cl.
*A61K 49/04* (2006.01)
*A61F 2/01* (2006.01)

(52) U.S. Cl.
CPC ............ *A61K 49/0438* (2013.01); *A61F 2/01* (2013.01)

(58) Field of Classification Search
CPC ............................. A61K 49/0438; A61F 2/01
See application file for complete search history.

(56) References Cited

U.S. PATENT DOCUMENTS

| | | | |
|---|---|---|---|
| 3,660,464 A | 5/1972 | Bernstein et al. | |
| 5,593,660 A | 1/1997 | Krause et al. | |
| 5,622,687 A | 4/1997 | Krishnan et al. | |
| 7,771,705 B2 | 8/2010 | Zhao | |
| 2005/0036946 A1 | 2/2005 | Pathak et al. | |
| 2007/0248547 A1 | 10/2007 | Brasch et al. | |
| 2008/0181847 A1* | 7/2008 | Robillard | A61K 47/665 424/1.11 |
| 2008/0228124 A1* | 9/2008 | Lamps | B01D 15/00 604/5.04 |
| 2016/0346409 A1* | 12/2016 | Valliant | A61K 49/223 |

FOREIGN PATENT DOCUMENTS

| | | |
|---|---|---|
| WO | 9310824 | 6/1993 |
| WO | 2008101166 | 8/2008 |
| WO | 2011140392 | 11/2011 |
| WO | 2012001532 | 1/2012 |
| WO | 2015033092 | 3/2015 |
| WO | 2015154082 | 10/2015 |
| WO | 2016055812 | 4/2016 |

OTHER PUBLICATIONS

Liu, Hui et al., "Ultrafast Click Chemistry wiht Fluorosydnones," Angew. Chem. Int. Ed. Engl. 2016, 55(39). (5 pages).
Ramil, Carlo P. et al., "Bioorhogonal Chemistry: strategies and recent development," Chem Commun (Camb). Dec. 7, 2013; 49(94): 11007-11022 (30 pages).
Bjerknes, Matthew et al., "Facile Quenching and Spatial Patterning of Cyclooctynes via Strain-Promoted Alkyne-Azide Cycloaddition of Inorganic Azides," Bioconjugate Chem. 2017, 28, 1560-1565 (6 pages).
Buncherd, Hansuk et al., "Selective Enrichment and Identification of Cross-Linked Peptides to Study 3-D Structures of Protein Complexes by Mass Spectrometry," Journal of Proteomics 75 (2012) 2205-2215 (11 pages).
Chang, Hyeonsoo et al., "Whole Blood Reflectance for Assessment of Hematologic Condition and Detection of Angiographic Contrast Media," Applied Optics, May 1, 2009, vol. 48 No. 13, 2435-2443 (9 pages).
International Search Report and Written Opinion for PCT Application No. PCT/US2019/018007 dated Jun. 19, 2019 (18 pages).
Parrillo, Viviana et al., "Catalyst-Free "Click" Functionalization of Polymer Brushes Preserves Antifouling Properties Enabling Detection in Blood Plasma," Analytica Chimica Acta. Jun. 8, 2017;971:78-87 (10 pages).
Santra, Santimukul et al., "Aliphatic Hyperbranched Polyester: A New Building Block in the Construction of Multifunctional Nanoparticles and Nanocomposites," Langmuir 2010, 26(18), 5364-73 (10 pages).
International Preliminary Report on Patentability for PCT Application No. PCT/US2019/018007 dated Sep. 24, 2020 (11 pages).
"Response to Communication Pursuant to Rules 161(1) and 162 EPC," for European Patent Application No. 19707638.3 filed May 12, 2021 (12 pages).

\* cited by examiner

*Primary Examiner* — Michael G. Hartley
*Assistant Examiner* — Leah H Schlientz
(74) *Attorney, Agent, or Firm* — Pauly, DeVries Smith & Deffner LLC

(57) ABSTRACT

An imaging contrast composition comprising an iodinated contrast agent and a ligand secured to the iodinated contrast agent is disclosed, the ligand comprising a reactive group capable of bonding to a capture substrate. A method of removing iodinated radiocontrast agents from a patient is disclosed, the method comprising providing an iodinated radiocontrast agent containing a reactive group; providing a capture substrate for insertion into a patient's bloodstream; administering the iodinated radiocontrast agent to the patient; conducting procedure CT scan or procedure using fluoroscopy; and sequestering the iodinated radiocontrast agent on the capture substrate.

7 Claims, 6 Drawing Sheets

RADIOCONTRAST AGENTS, SCAVENGING METHODS, AND SCAVENGING SYSTEM

This application claims the benefit of U.S. Provisional Application No. 62/641,682, filed Mar. 12, 2018, the content of which is herein incorporated by reference in its entirety.

FIELD OF THE INVENTION

The present technology generally relates to iodinated radiocontrast agents, including iodinated radiocontrast agents modified to be scavenged from a patient, as well as methods and systems for scavenging iodinated radiocontrast agents from a patient.

BACKGROUND

Contrast agents are commonly used in computerized tomography scans ("CT scans") and fluoroscopy. Iodinated radiocontrast agents are one of the more commonly used contrast agents. Iodinated radiocontrast agents and their byproducts are often excreted unchanged by glomerular filtration. However, the relatively large amounts of contrast agent (often 50 to 200 mL of solution per fluoroscopy) can cause complications for patients. For example, the excess contrast agent can lead to serious conditions such as thyroid dysfunction (including hyperthyroidism and hypothyroidism) and contrast induced nephropathy in susceptible patients (e.g. type-II diabetics, patients with CKD, etc.)

Therefore, a need exists for a way to effectively remove iodinated radiocontrast agents from a patient's bloodstream after undergoing CT scan procedures or procedures using fluoroscopy.

SUMMARY

Embodiments include functionalized iodinated contrast agents, systems for removing iodinated contrast agent from a patient, and methods for removing iodinated contrast agent from a patient.

In a first aspect, a functional iodinated radiocontrast agent includes a ligand secured to the iodinated radiocontrast contrast agent, the ligand comprising a reactive group capable of bonding to a capture molecule on a capture substrate.

In a second aspect, in addition or in place of other aspects herein, the ligand secured to the iodinated contrast agent comprises a plurality of amine groups.

In a third aspect, in addition or in place of other aspects herein, the ligand secured to the iodinated contrast agent comprises a plurality of acid groups.

In a fourth aspect, in addition or in place of other aspects herein, the reactive group on the ligand comprises an azide group.

In a fifth aspect, in addition or in place of other aspects herein, the reactive group on the ligand comprises an azide, alkyne, tetrazine, fluorosydnones, or combinations thereof.

In a sixth aspect, in addition or in place of other aspects herein, the capture substrate comprises a strained alkyne.

In a seventh aspect, in addition or in place of other aspects herein, the strained alkyne of the capture substrate is selected from the group OCT (cyclooctyne), DIMAC (dimethoxyazacyclooctyne), DIFO (difluorinated cyclooctynes), BCN (bicyclo[6.1.0]nonyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne) and mixtures thereof.

In an eighth aspect, in addition or in place of other aspects herein, the functionalized iodinated radiocontrast agent forms a covalent bond with the capture molecule on the capture substrate.

In a ninth aspect, in addition or in place of other aspects herein, the functionalized iodinated radiocontrast agent and the capture molecule form a tri-azole ring.

In a tenth aspect, in addition or in place of other aspects herein, a system for removing iodinated radiocontrast agent from a patient includes an iodinated radiocontrast agent secured to a ligand comprising a reactive group capable of bonding to a capture molecule on a capture substrate; and a capture substrate containing a capture molecule that forms a bond with the reactive group on the iodinated radiocontrast agent.

In an eleventh aspect, in addition or in place of other aspects herein, the reactive group on the ligand comprises an azide group.

In a twelfth aspect, in addition or in place of other aspects herein, the iodinated contrast agent secured to a ligand comprises an azide reactive group; and the capture substrate comprises a polymer containing a strained alkyne; the strained alkyne selected from the group OCT (cyclooctyne), DIMAC (dimethoxyazacyclooctyne), DIFO (difluorinated cyclooctynes), BCN (bicyclo[6.1.0] nonyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne) and mixtures thereof.

In a thirteenth aspect, in addition or in place of other aspects herein, the capture substrate comprises a textile, foam, or web.

In a fourteenth aspect, in addition or in place of other aspects herein, a method of removing iodinated radiocontrast agents from a patient includes providing an iodinated radiocontrast agent comprising a reactive group; providing a removable capture substrate containing a capture molecule that bonds to the reactive group of the iodinated radiocontrast agent; administering the iodinated radiocontrast agent to a patient to visualize various circulatory vessels and heart anatomy or perform a CT scan; and sequestering the iodinated radiocontrast agent on the removable capture substrate.

In a fifteenth aspect, in addition or in place of other aspects herein, the removable capture substrate is positioned upstream of the kidney of the patient during sequestration of the iodinated radiocontrast agent.

In a sixteenth aspect, in addition or in place of other aspects herein, the ligand secured to the iodinated contrast agent comprises a plurality of amine groups.

In a seventeenth aspect, in addition or in place of other aspects herein, the reactive group on the ligand comprises an azide group.

In an eighteenth aspect, in addition or in place of other aspects herein, the reactive group on the ligand comprises an azide, alkyne, tetrazine, fluorosydnones, or combinations thereof.

In a nineteenth aspect, in addition or in place of other aspects herein, the capture substrate comprises a strained alkyne.

In a twentieth aspect, in addition or in place of other aspects herein, the strained alkyne of the capture substrate is selected from the group OCT (cyclooctyne), DIMAC (dimethoxyazacyclooctyne), DIFO (difluorinated cyclooctynes), BCN (bicyclo[6.1.0] nonyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne) and mixtures thereof.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense.

BRIEF DESCRIPTION OF THE DRAWINGS

The present subject matter may be more completely understood and appreciated in consideration of the following detailed description of various embodiments in connection with the accompanying drawings.

While embodiments herein are susceptible to various modifications and alternative forms, specifics thereof have been shown by way of example and drawings and will be described in detail. It should be understood, however, that the scope herein is not limited to the particular examples described. On the contrary, the intention is to cover modifications, equivalents, and alternatives falling within the spirit and scope herein.

DETAILED DESCRIPTION

Iodinated contrast agents are used for imaging during medical procedures, such as the blood vessels or heart for stent placement, valve placement, confirmation of catheter placement, etc. Although iodinated radiocontrast agents and their byproducts are mostly excreted unchanged by glomerular filtration, studies have shown the contrast agent and byproduct accumulates in tissues, such as brain, bone, and kidneys.

The present disclosure is directed to iodinated radiocontrast agents that have been modified to provide a functional group that can covalently bond, for example spontaneously bond, to a capture molecule secured to a removable substrate and then removed from a patient. The bond between the iodinated radiocontrast agent and the capture molecule allows for subsequent removal of the iodinated radiocontrast agent by removal of the substrate containing the capture molecules. More specifically, water-soluble (and typically iso-osmolar) iodine-based contrast agents are modified with functional groups so that the contrast agent can selectively, rapidly react with a biorthogonal counterpart capture molecule secured to a substrate, and this substrate can then be removed from the patient. As such, the iodinated radiocontrast agents and reactive substrate utilize "click chemistry" to selectively and effectively remove the iodinated radiocontrast agents.

Figure 1:
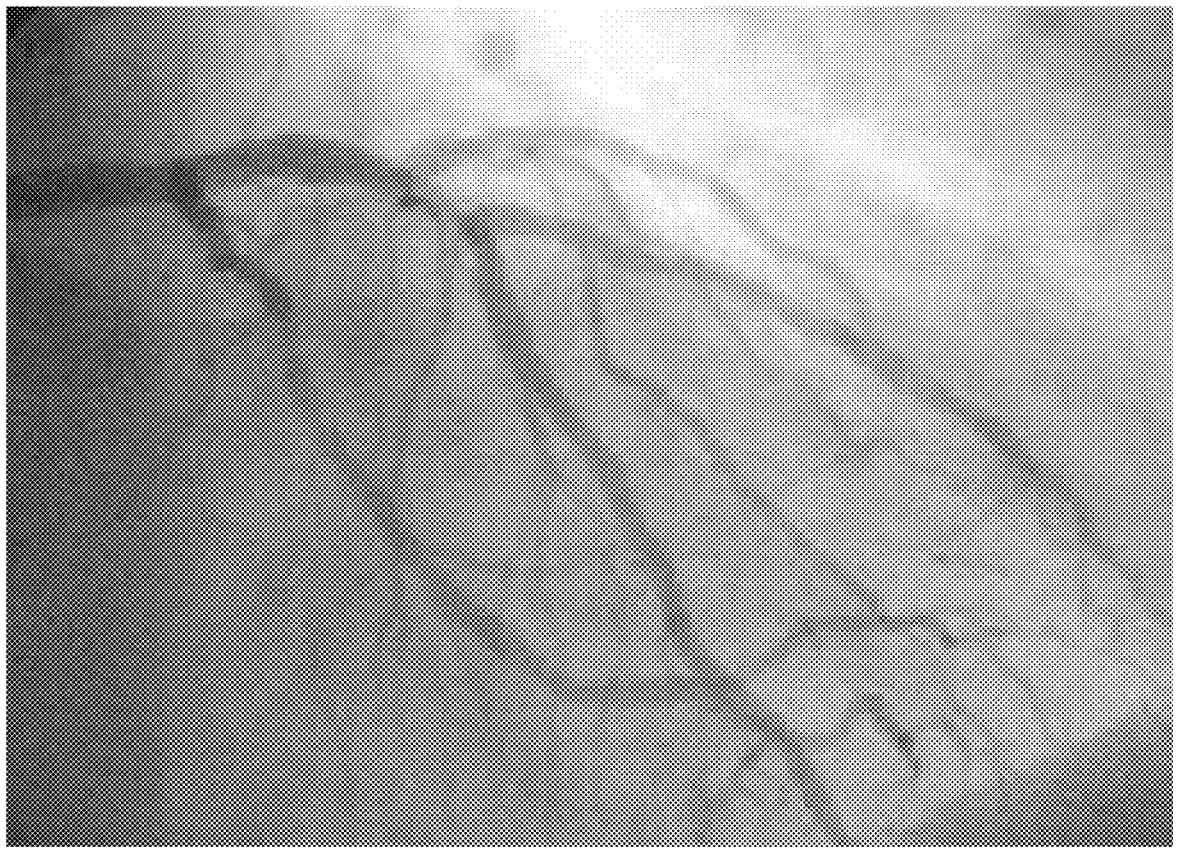
FIG. 1 shows a fluoroscopy image of human blood vessels using an iodinate-based radiocontrast agent.

Referring now to the drawings, FIG. 1 shows a fluoroscopy image of a human heart, with iodinated radiocontrast agent used to make the blood vessels more visible. As can be seen in FIG. 1, the contrast agent provides improved imaging.

The iodinated radiocontrast agent can be modified to add a reactive group capable of bonding to a capture substrate. One example modification is to add an azide group to the iodine ligand. An azide group is particularly useful because it is small, metabolically stable, and does not naturally exist in cells. Thus, it has no competing biological side reactions.

Figure 2A:
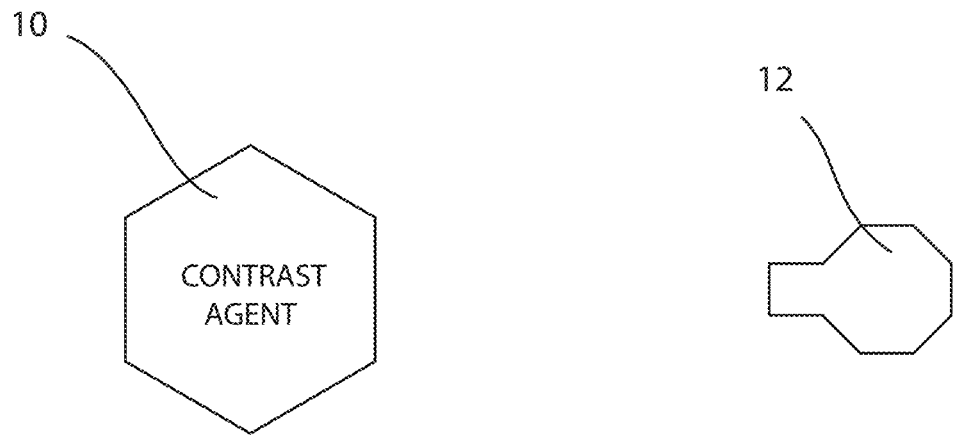
FIG. 2A is a schematic diagram of an iodinate-based radiocontrast agent prior to addition of a reactive group.
Figure 2B:
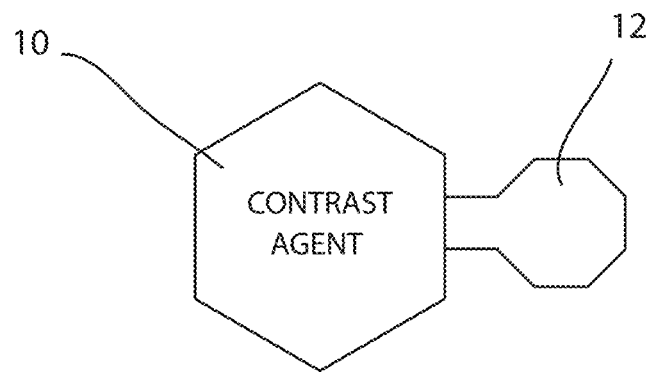
FIG. 2B is a schematic diagram of an iodinate-based radiocontrast agent after addition of a reactive group.

FIG. 2A is a schematic of an iodinated radiocontrast agent 10 prior to addition of the reactive group 12, and FIG. 2B is a schematic of an iodinated radiocontrast agent 10 after addition of a reactive group 12. FIG. 2B shows the iodinated radiocontrast agent 10 with the reactive group 12, such as an azide, attached.

An example of a specific linear iodinated radiocontrast agent to which an azide can be attached is reproduced below, showing iodixanol with central alcohol group that can be modified to add an azide.

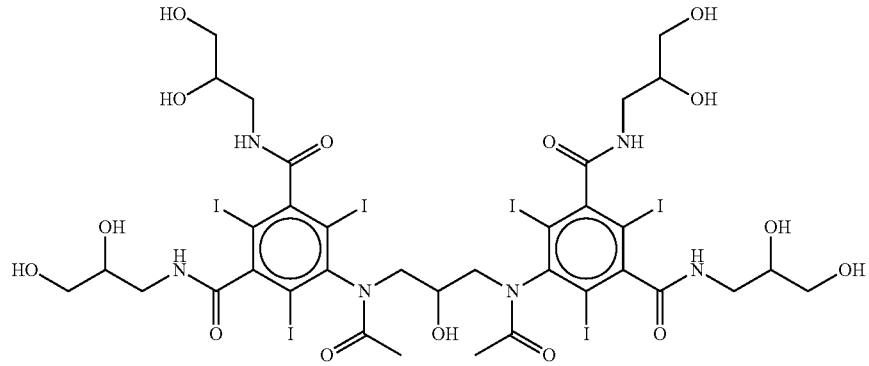

Figure 3:
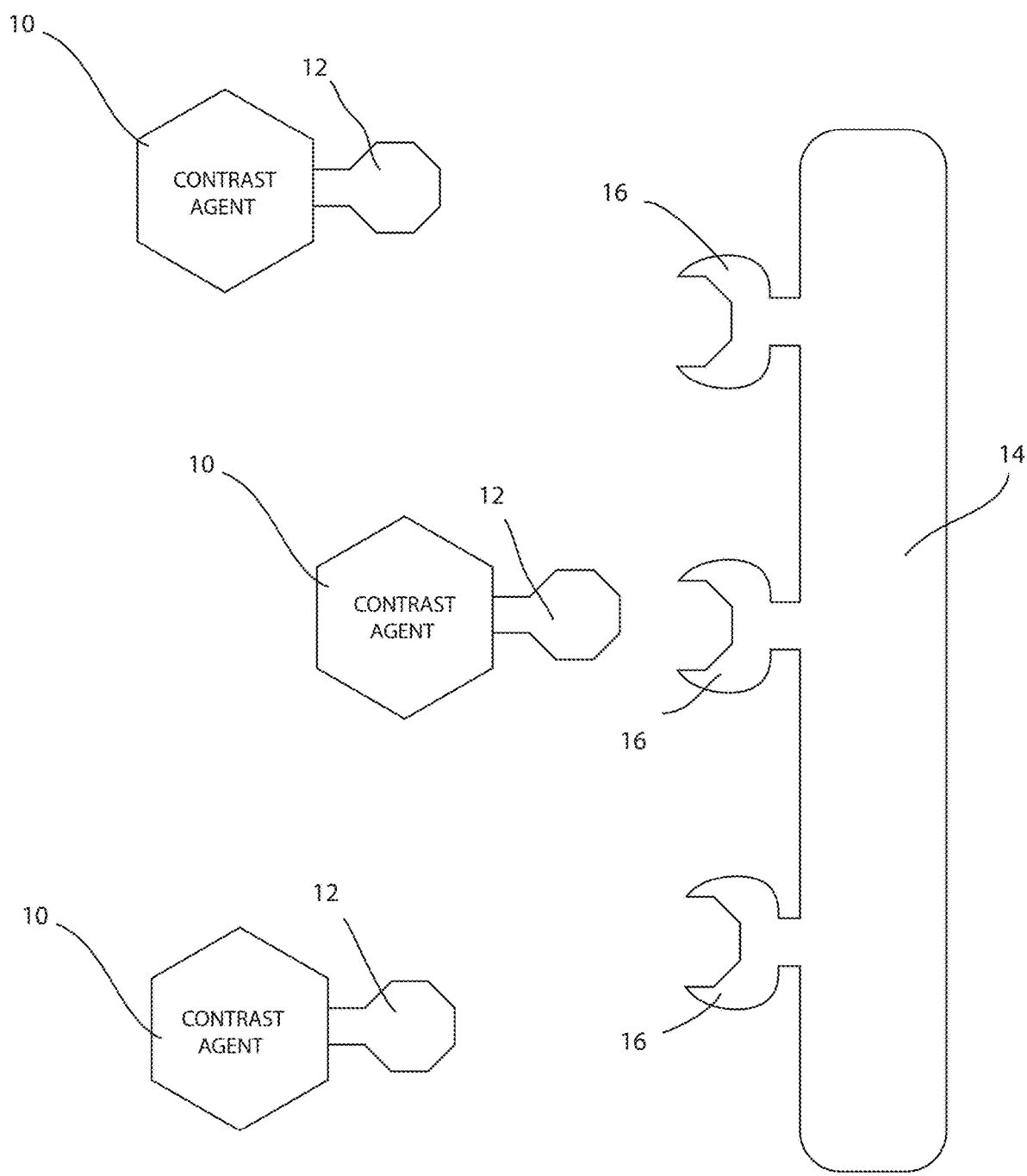
FIG. 3 is a schematic diagram of iodinate-based radiocontrast agents to which reactive groups have been added, shown with a reactive substrate.

Referring now to FIG. 3, a schematic representation is shown of multiple iodinated radiocontrast agent molecules 10 from FIG. 2 with reactive groups 12 (such azides), along with a capture substrate 14. The capture substrate 14 includes capture molecules 16, such as strained alkynes, capable of an irreversible reaction, for example a spontaneous irreversible reaction, with reactive groups 12. The capture molecules 16 are shown secured to the capture substrate 14, but without any of the contrast agent molecules 10 yet reacted with the capture molecules 16.

Figure 4:
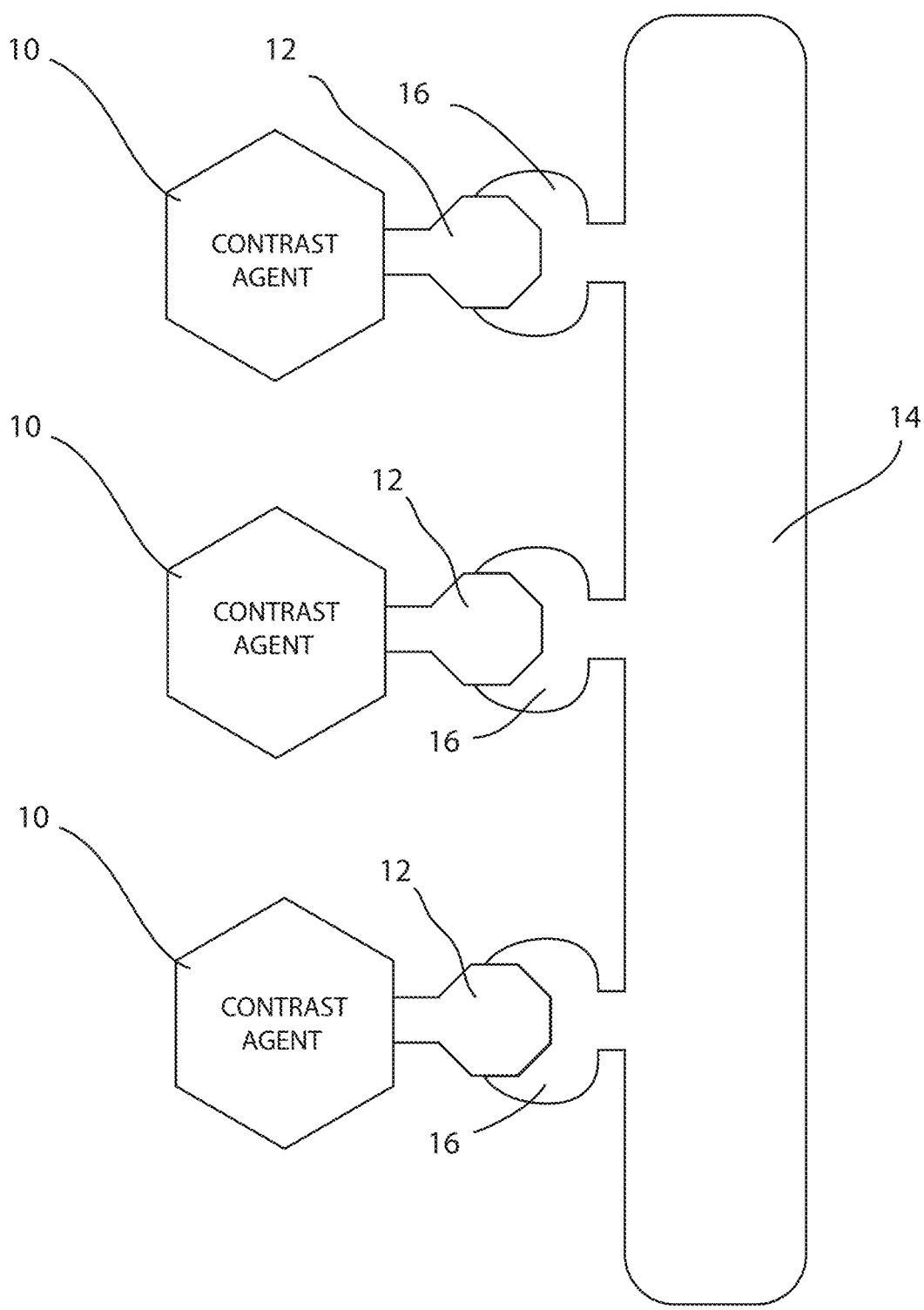
FIG. 4 is schematic diagram of iodinated radiocontrast agents to which reactive groups have been added, showing the iodinated radiocontrast agents sequestered on a reactive substrate.

FIG. 4 is a schematic of iodinated radiocontrast agents 10 to which reactive groups 12 have been added, showing the iodinated radiocontrast agents 10 sequestered on the capture substrate 14 by way of the "locks" and reactive groups 12 of the contrast agent 10 having reacted with the capture molecules 16 of the capture substrate 14. The capture substrate 14 can be, for example, a polymeric film, fabric, foam, mesh or other material to which the capture molecules 16 have been secured. After the capture molecules 16 bind to iodinated radiocontrast agents 10, the entire substrate 14 and accompanying bonded iodinated radiocontrast agents 10 can be removed from a patient. The removal from the patient of the radiocontrast agents 10 can occur using a removal device (also referred to as a filter) that is external or internal to the patient's body. In some implementations multiple removal devices are used, both internal and external to the patient's body.

Synthesis of an example linear or open chain iodinated radiocontrast agent is shown below (without the iodinated contrast agent present):

The iodinated radiocontrast agents are modified to add a reactive group capable of bonding to a capture substrate. One example modification is to add an azide group to the iodine ligand. More generally, the reactive group of the ligand can be, for example, an azide, alkyne, tetrazine, fluorosydnones, or combinations thereof. The azide group is particularly appropriate because it is small, metabolically stable, and does not naturally exist in cells. Thus, it has no competing biological side reactions. The alkyne is not as small as the azide group, but it has the stability and orthogonality necessary for in vivo labeling. Desired properties for the ligand comprising the reactive group and the related capture substrate include strong selectivity, generally biological inertness, generally chemical inertness, favorable kinetics, and reaction biocompatibility. With regard to selectivity, it is desirable that the reaction be selective between functional groups to avoid side reactions with biological compounds. With regard to biological inertness, desirably the reactive group on the contrast ligand should not possess reactivity capable of disrupting the native chemical functionality of the patient. Regarding chemical inertness, the covalent link between the reactive group on the ligand and the capture molecule on the capture substrate should be strong and inert to biological reactions.

The following two reactions show a manner in which an azide group can be added during formation of an iodixanol analog, first showing the formation of standard iodixanol, and then the analog that has the azide group added:

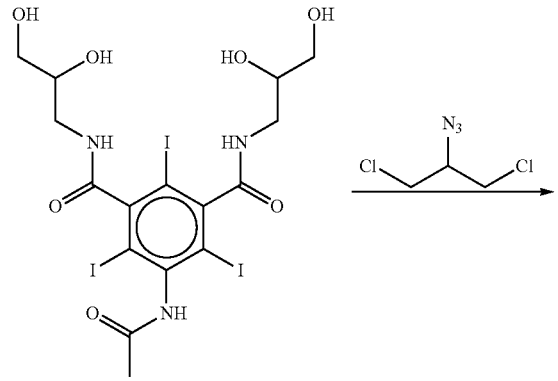

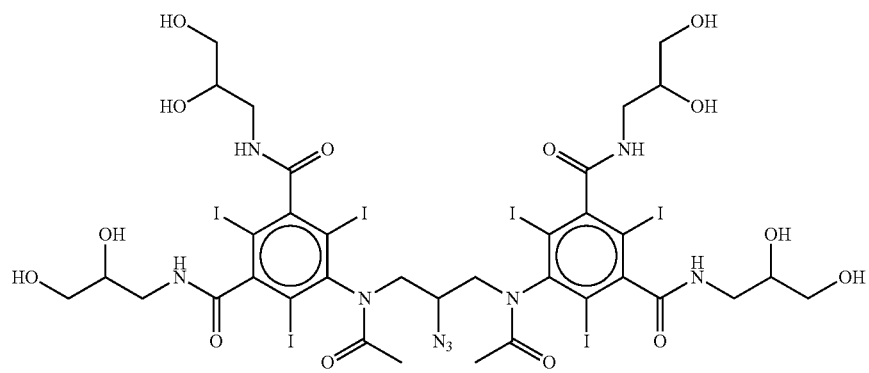

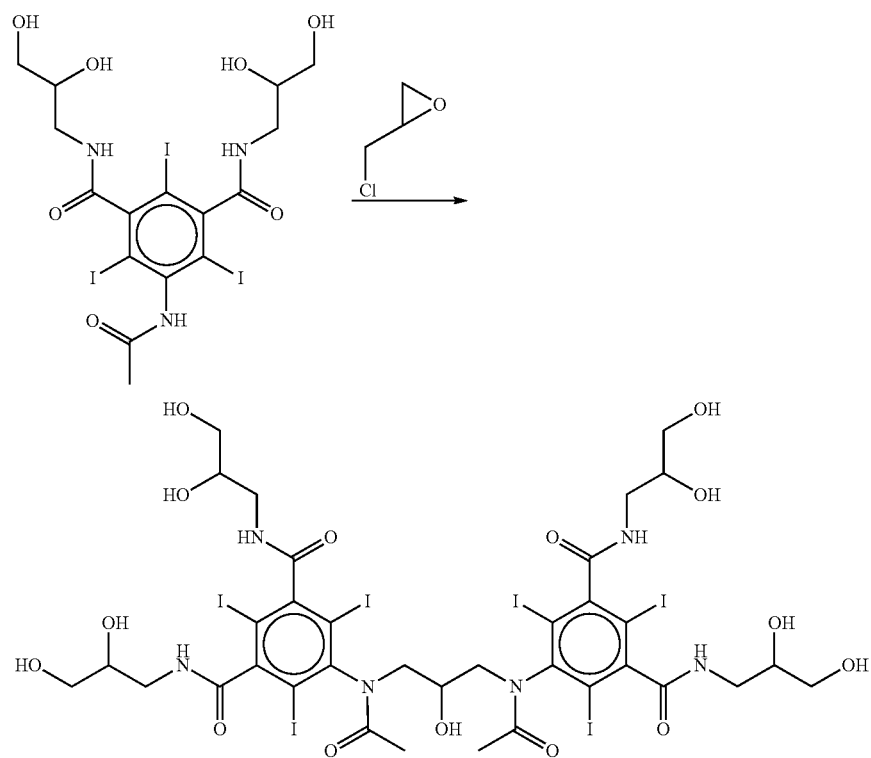
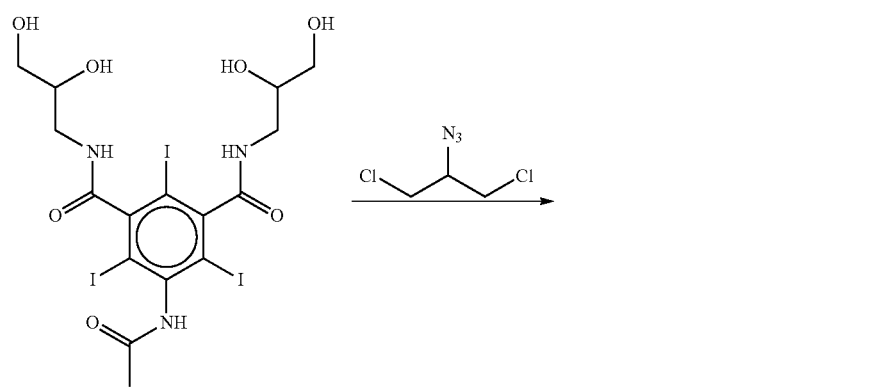
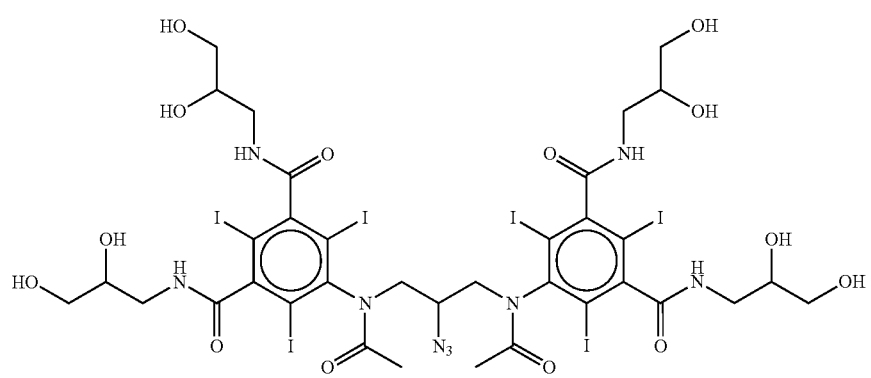

-continued

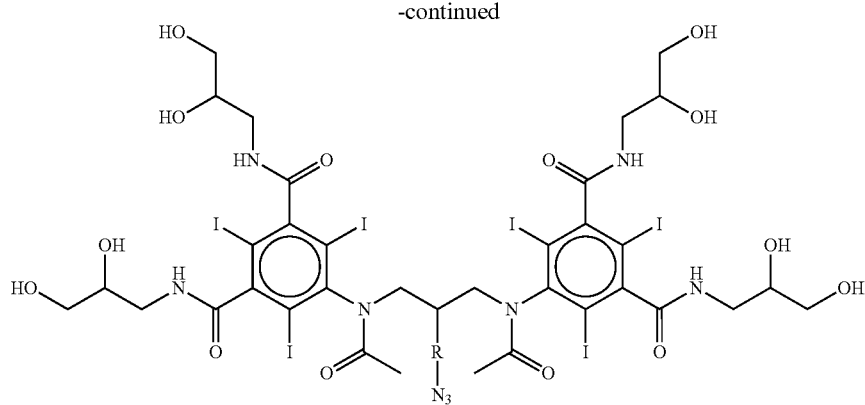

The reactive group of the iodinated radiocontrast agent is reactive with groups on the capture substrate. The capture substrate can be, for example, a substrate or polymer having exposed strained alkyne functional groups. The reactive receptor group can be, for example, OCT (cyclooctyne), DIMAC (dimethoxyazacyclooctyne), DIFO (difluorinated cyclooctynes), BCN (bicyclo[6.1.0] nonyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne); monofluorinated cyclooctyne, and mixtures thereof. Norborenene is an additional alternative that is not an alkyne. Due to the bulky ligands, reaction kinetics can be increased by making the azide more available. The R can be, for example, a 0-4 alkyl or aryl group.

An example of a biorthogonal, strain-promoted azide-alkyne cycloaddition ("SPAAC) is shown below:

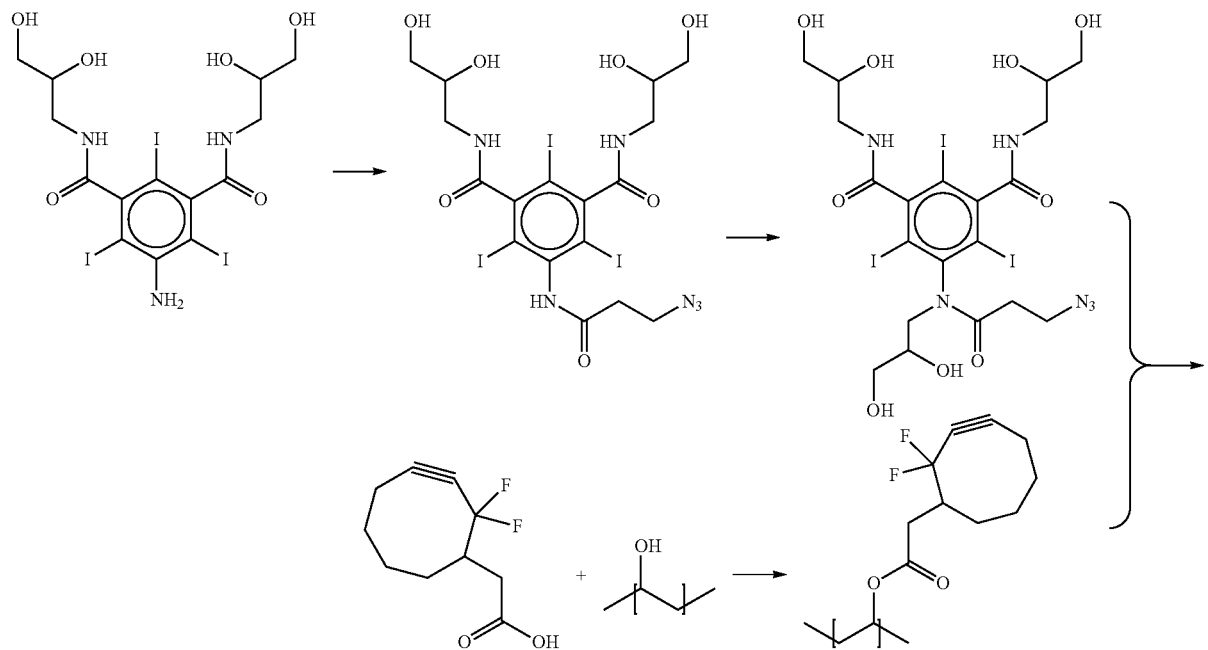

-continued

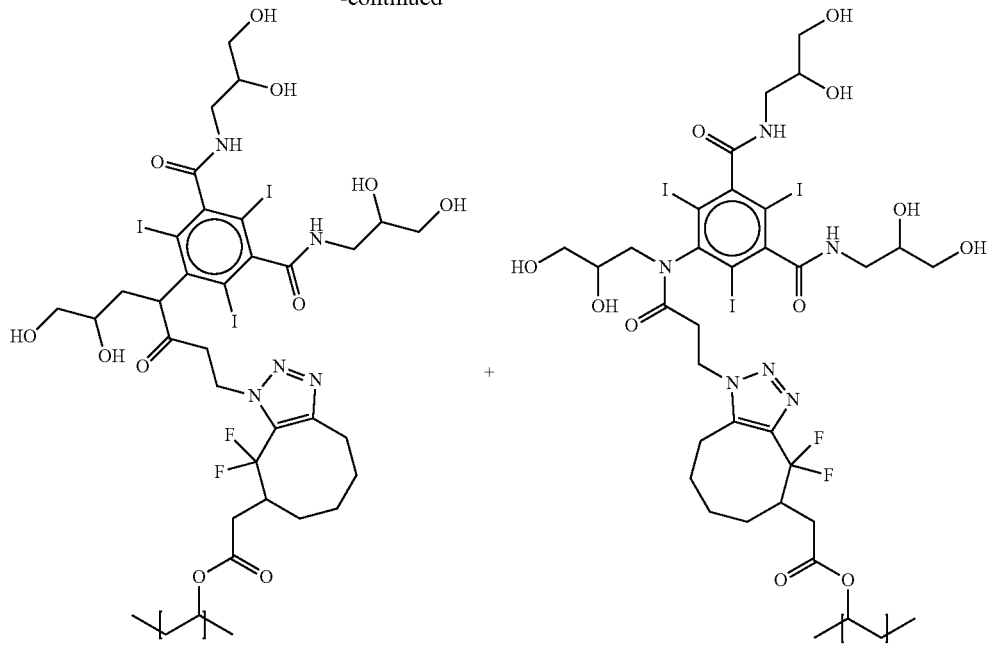

The functionalized iodinated radiocontrast agent forms, such as spontaneously, a covalent bond with the capture substrate. In some embodiments the functionalized iodinated radiocontrast agent and the capture substrate form a tri-azole ring.

The reaction can be refined to promote increased speed and capture yield, such as with the following reaction:

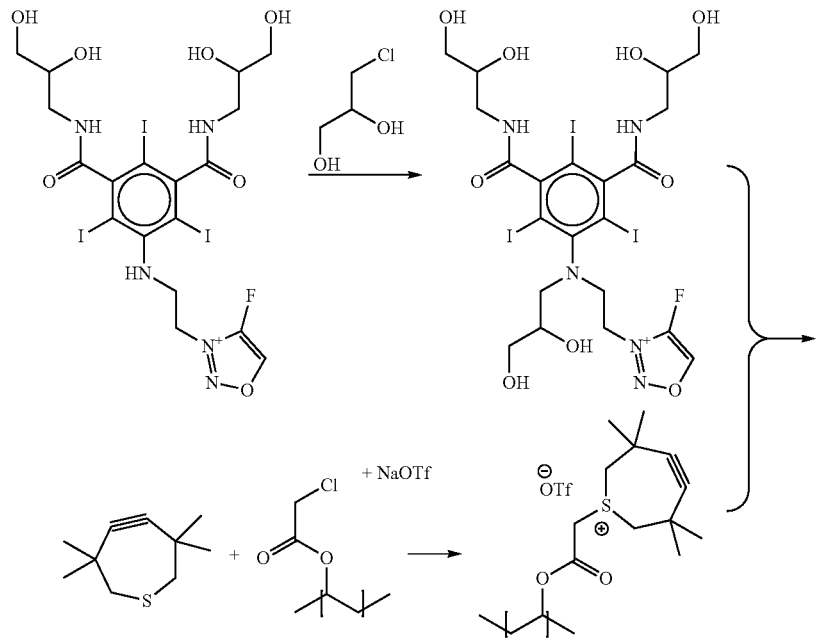

-continued

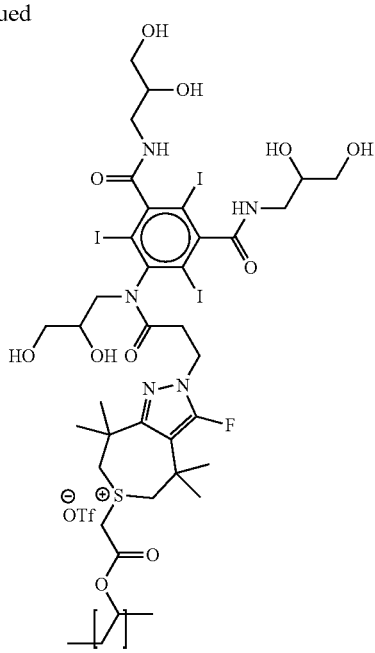

The capture substrate can include, for example, a textile, sponge, or gel. The capture substrate is, for example, porous. Suitable capture substrates include, for example, polyvinyl alcohol (PVA) to which the capture molecule (such as a moiety containing a strained alkyne) has been secured. The modified iodinated radiocontrast agent is brought in contact with the substrate during and after the CT scan or fluoroscopy procedure, such as by insertion into a blood vessel or retained in a chamber outside of the body but through which blood is passed.

A further example capture reaction includes:

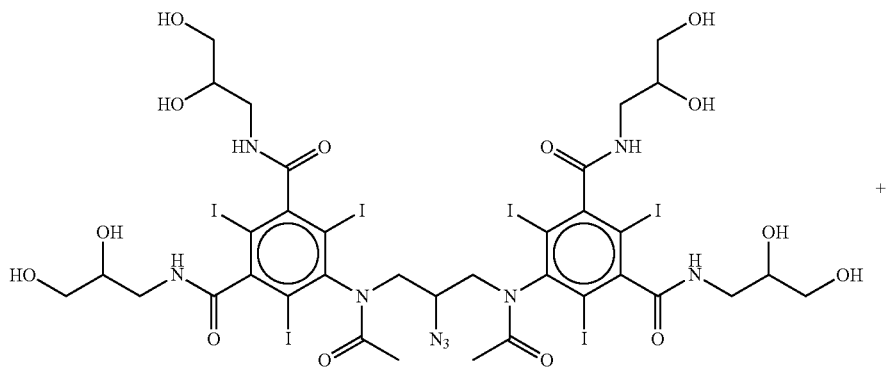

+

-continued

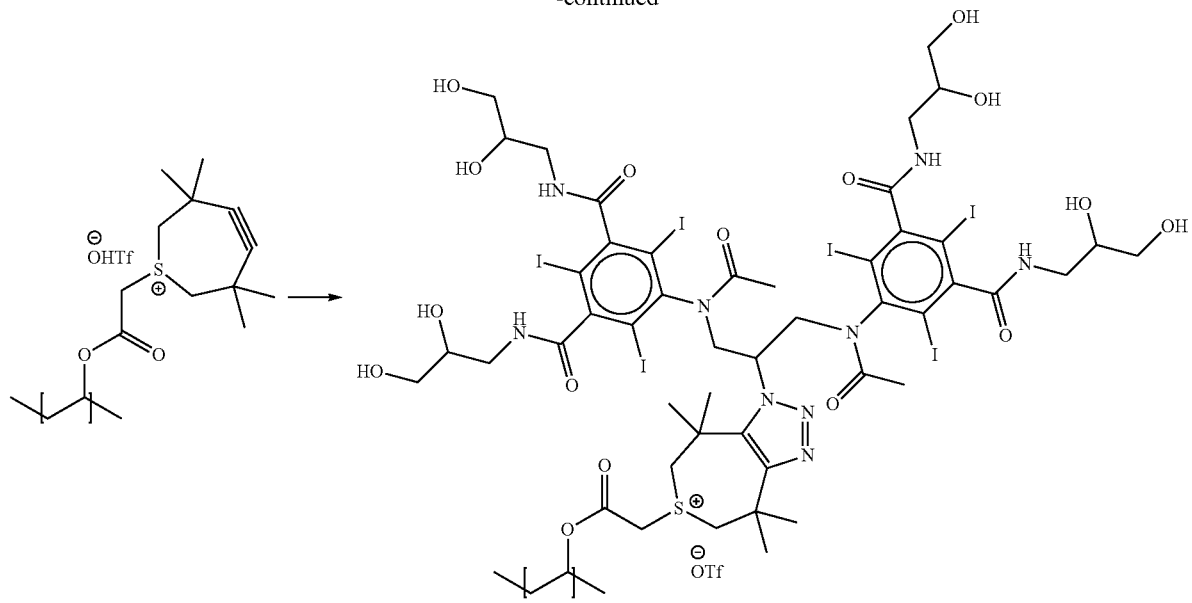

The iodinated radiocontrast agents described herein can be used as part of a method of removing iodinated radiocontrast agents from a patient, the method comprising providing an iodinated radiocontrast agent having a reactive group; providing a removable capture substrate; administering the iodinated radiocontrast agent to the patient; conducting a magnetic resonance imaging procedure; and sequestering the iodinated radiocontrast agent on the removable capture substrate. Thereafter the capture substrate is removed from the patient.

The iodinated radiocontrast agent can be captured and removed as part of a system comprising an iodinated contrast agent secured to a ligand comprising a reactive group capable of bonding to a capture substrate; and a capture substrate. The iodinated contrast agent secured to a ligand can include an azide reactive group; and the capture substrate can include a polymer containing a strained alkyne; the strained alkyne selected from the group OCT (cyclooctyne), DIMAC (dimethoxyazacyclooctyne), DIFO (difluorinated cyclooctynes), BCN (bicyclo[6.1.0]nonyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne) and mixtures thereof.

Figure 5:
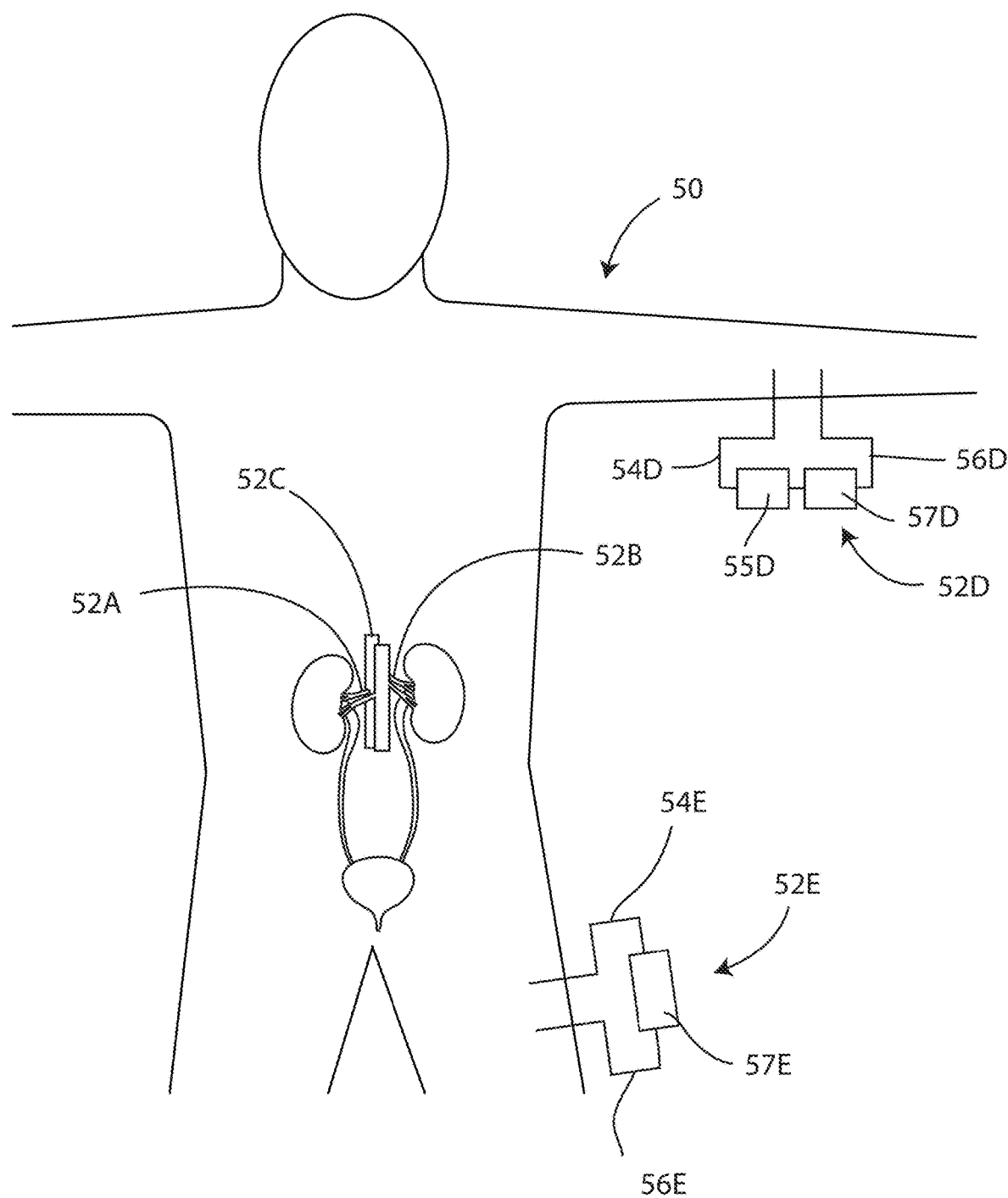
FIG. 5 is a schematic diagram showing example locations of iodinated contrast agent scavenger positioned inside and outside a patient's body.

Now, in reference to FIG. 5, a schematic diagram of a patient 50 shows example locations 52A, 52B, 52C, 52D and 52E for an iodinated contrast agent scavenger. Patient 50 is shown as a human outline, but examples are not so limited and may include any mammalian. FIG. 5 is simplified and not drawn to scale, showing body organs and scavenger systems schematically only. The locations 52A to 52E are shown for illustrative purposes, indicating how the location of the contrast agent scavenger can be varied. Locations 52A, 52B and 52C are all internal locations in which the contrast scavenger agent is inserted into a blood vessel, typically a blood vessel upstream of one or both kidneys. For example, locations 52A and 52B show locations at the right and left renal arteries, respectively, while location 52C is in the inferior vena cava. In such implementations the iodinated contrast agent scavenger can be applied in the form of a textile, membrane, foam, gel, web or other substance inserted into the blood vessel and then removed after the medical procedure is completed and adequate contrast agent has been scavenged.

FIG. 5 also shows schematic representations of two external locations 52D and 52E for removing iodinated contrast agents from the patient 50. Location 52D is shown on a peripheral body location, with an intravenous catheter 54D leading to an optional pump 55D that flows into a sequestering element 57D and then back into the patient 50 by way of intravenous catheter 56D. The sequestering element 57D contains a textile, membrane, foam, gel, web or other substance with exposed sequestering agent for binding the iodinated contrast agent. Alternative location 52E for removing iodinated contrast agents includes intravenous catheter 54E leading to sequestering element 57E and then flow out through return catheter 56E. Location 52E is depicted without an auxiliary pump, although generally some sort of mechanism is used to apply adequate pressure to return the blood to the patient.

External positioning of the contrast agent scavenger at location 52D and 52E are less invasive than inserting the contrast agent scavenger into locations 52A, 52B or 52C, but is also typically slower to remove the contrast agent and allows initial exposure of the kidneys to higher levels of contrast agent. It is contemplated, that one or any combination of example locations 52A, 52B, 52C, 52D, and 52E can be used for an iodinated contrast agent scavenger.

Figure 6:
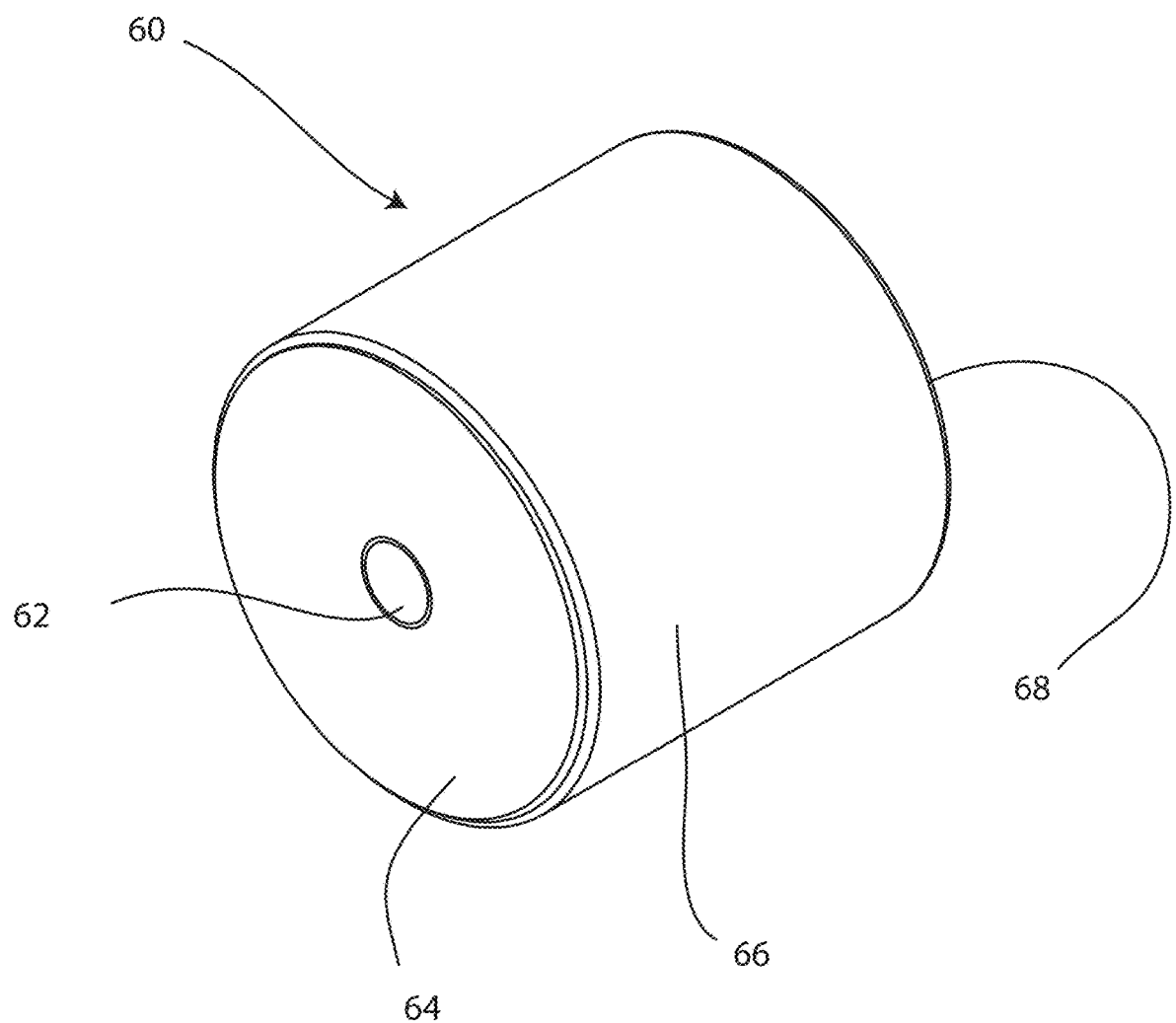
FIG. 6 is a perspective view of an article containing an iodinated contrast agent scavenger configured for the flow of blood through the article to retain the iodinated contrast agent.

FIG. 6 is a perspective view of iodinated capture element 60 containing an iodinated contrast agent scavenger configured for the flow of blood through the element to retain the iodinated contrast agent such as elements 57D and 57E of FIG. 5. The capture element 60 includes a housing 66, along with an inlet 62 on a first end 64 of the housing 66 for receiving blood containing iodinated contrast agent, plus an outlet (not shown) opposite the inlet 62 on the second end 68 of the housing, through which the blood exits the housing 66. Within the housing 66 is capture media. The capture media contains capture substrate as described herein, such as a capture substrate having exposed strained alkynes available for reacting with functionalized iodinated contrast agent, such as iodinated functionalized with an azide group.

It should also be noted that, as used in this specification and the appended claims, the phrase "configured" describes a system, apparatus, or other structure that is constructed to perform a particular task or adopt particular characteristics. The phrase "configured" can be used interchangeably with other similar phrases such as "arranged", "arranged and configured", "programmed" "constructed and arranged", "constructed", "manufactured and arranged", and the like.

All publications and patent applications in this specification are indicative of the level of ordinary skill in the art to which the present technology pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive.

We claim:

1. A method of removing iodinated radiocontrast agents from a patient, the method comprising:
   providing an iodinated radiocontrast agent comprising a ligand containing a reactive group capable of covalently bonding irreversibly to a biorthogonal capture molecule on a removable capture substrate;
   providing a removable capture substrate comprising a polymeric film, gel, web, fabric, foam, mesh or other material to which capture molecules have been secured, the capture substrate containing the capture molecule that bonds to the reactive group of the iodinated radiocontrast agent;
   administering the iodinated radiocontrast agent to a patient to visualize various circulatory vessels and heart anatomy or perform a CT scan;
   sequestering the iodinated radiocontrast agent on the removable capture substrate by irreversibly covalently bonding the reactive group of the iodinated radiocontrast agent to the biorthogonal capture molecule; and
   removing the capture substrate and sequestered iodinated radiocontrast agent from the patient without passing the capture substrate through the patient's kidney.

2. The method of claim 1, wherein the removable capture substrate is positioned upstream of the kidney of the patient during sequestration of the iodinated radiocontrast agent.

3. The method of claim 1, wherein the ligand secured to the iodinated contrast agent comprises a plurality of amine groups.

4. The method of claim 1, wherein the reactive group on the ligand comprises an azide group.

5. The method of claim 1, wherein the reactive group on the ligand comprises an azide, alkyne, tetrazine, fluorosydnones, or combinations thereof.

6. The method of claim 1, wherein the capture substrate comprises a strained alkyne.

7. The method of claim 6, wherein the strained alkyne of the capture substrate is selected from the group OCT (cyclooctyne), DIMAC (dimethoxyazacyclooctyne), DIFO (difluorinated cyclooctynes), BCN (bicyclo[6.1.0] nonyne), DIBO (dibenzocyclooctyne), DIFBO (difluorobenzocyclooctyne), DIBAC aza-dibenzocyclooctyne), BARAC (biarylazacyclooctynone), TMTH (3,3,6,6-tetramethyl-thiacycloheptyne) and mixtures thereof.

* * * * *